tion period.

(12) United States Patent
Hoshino et al.

(10) Patent No.: US 7,432,076 B2
(45) Date of Patent: Oct. 7, 2008

(54) ASTAXANTHIN PRODUCTION USING FED-BATCH FERMENTATION PROCESS BY PHAFFIA RHODOZYMA

(75) Inventors: Tatsuo Hoshino, Kanagawa-ken (JP); Yutaka Setoguchi, Kanagawa-ken (JP); Yoshinori Takagi, Kanagawa-ken (JP)

(73) Assignee: DSM IP Assets B.V., TE Heerlen (NL)

( * ) Notice: Subject to any disclaimer, the term of this patent is extended or adjusted under 35 U.S.C. 154(b) by 265 days.

(21) Appl. No.: 10/528,871

(22) PCT Filed: Sep. 16, 2003

(86) PCT No.: PCT/EP03/10293

§ 371 (c)(1),
(2), (4) Date: Sep. 30, 2005

(87) PCT Pub. No.: WO2004/029260

PCT Pub. Date: Apr. 8, 2004

(65) Prior Publication Data

US 2006/0134734 A1      Jun. 22, 2006

(30) Foreign Application Priority Data

Sep. 27, 2002 (EP) ................................ 02021604

(51) Int. Cl.
*C12P 23/00* (2006.01)
(52) U.S. Cl. ........................................................ 435/67
(58) Field of Classification Search .................... 435/67
See application file for complete search history.

(56) References Cited

U.S. PATENT DOCUMENTS 6,015,684 A      1/2000   Jacobson et al.

FOREIGN PATENT DOCUMENTS

KR      2001044210 A  *  6/2001
WO      WO 88/08025      10/1988

OTHER PUBLICATIONS

Yamane, Y. et al., "Influence of Oxygen and Glucose on Primary Metabolism and Astaxanthin Production by *Phaffia rhodozyma* in Batch and Fed-Batch Cultures: Kinetic and Stoichiometric Analysis," *Applied and Environmental Microbiology*, vol. 63, No. 11, pp. 4471-4478 (1997).
Ho, K.P. et al., "Growth and Carotenoid Production of *Phaffia rhodozyma* in Fed-Batch Cultures with Different Feeding Methods," *Biotechnology Letters*, vol. 21, pp. 175-178 (1999).
Fell, J.W. and Blatt, G.M., "Separation of Strains of the Yeasts *Xanthophyllomyces dendrorhous* and *Phaffia rhodozyma* Based on rDNA IGS and ITS Sequence Analysis," *Journal of Industrial Microbiology and Biotechnology*, vol. 23, pp. 677-681 (1999).

* cited by examiner

*Primary Examiner*—Herbert J Lilling
(74) *Attorney, Agent, or Firm*—Bryan Cave LLP

(57) ABSTRACT

Disclosed is a fermentation method of astaxanthin using Phaffia rhodozyma comprising the steps of: (a) in the growing phase, feeding of a nutrient medium containing glucose or sucrose based on the specific growth rate (μ) of Phaffia rhodozyma cells, and (b) in the astaxanthin production phase, feeding of the nutrient medium based on the astaxanthin production rate, while keeping the glucose concentration in the fermentation broth almost 0 g/L during the whole fermentation period.

10 Claims, No Drawings

ASTAXANTHIN PRODUCTION USING FED-BATCH FERMENTATION PROCESS BY PHAFFIA RHODOZYMA

This application is the National Stage of International Application No. PCT/EP2003/010293, filed Sep. 16, 2003.

The present invention provides a process for producing astaxanthin in high yield by Phaffia rhodozyma (P. rhodozyma) utilizing the fed-batch fermentation system with application of new feeding methods based on the cell growth, the carbon source consumption and the carotenoids production.

Astaxanthin, as one of well-known carotenoids, is a xanthophyll commonly found as red or orange pigment in marine environments. Since this pigment is considered as a characteristic color in certain marine animals that cannot synthesize β-carotene de novo such as salmon, crustaceans and trouts, it is therefore necessary to add it to their diet in order to give them a suitable color that appeals to the consumer. This carotenoid is also useful for adding pigmentation to the flesh and products of other animals, and to other foodstuffs, e.g. poultry and eggs, various dairy products, snack foods, and the like. Only a few microorganisms synthesize astaxanthin, of which the yeast P. rhodozyma is a possible candidate for commercial production because of its high astaxanthin content. P. rhodozyma is known as a carotenogenic yeast strain which produces astaxanthin specifically. Different from the other carotenogenic yeast, *Rhodotorula* spec., P. rhodozyma can ferment some sugars such as D-glucose. This is an important feature from a viewpoint of industrial application. In a recent taxonomic study, a sexual cycle of P. rhodozyma was revealed and its telemorphic state was designated under the name of Xanthophyllomyces dendrorhous. However, natural isolates of P. rhodozyma produce so little astaxanthin (typically 100 to 300 parts per million (ppm)) that they are not practical or economical pigment sources for aquaculture. If Phaffia strains are to be an economically feasible feed additive for coloring aquatic animals, or any other potential food stuff (animal or otherwise), then astaxanthin over-producing strains must be developed. Mutants of naturally occurring "wild-type" Phaffia have been described in literature, allegedly capable of generating higher levels of astaxanthin than the wild-type yeasts. These strains reportedly produce higher levels of astaxanthin than the wild-type isolates under-specific conditions.

Besides the need to develop a suitable strain of P. rhodozyma for commercial carotenoids production, methods for cultivating P. rhodozyma also need to be developed which maximize carotenoids production in large fermentors.

The present invention provides a process for the production of astaxanthin in high yield comprising applying new feeding methods of nutrient media based on the cell growth, the carbon source consumption and the carotenoids productions in the fed-batch mode by Phaffia strains. Especially, by using the new feeding methods of nutrient media based on the carbon source consumption, the fermentation period could be shortened and the astaxanthin yield could be significantly enhanced The present invention relates to a fermentation process for production of astaxanthin in high yield by P. rhodozyma which applies the new feeding methods of nutrient media based on the cell growth, the carbon source consumption and the carotenoids productions in the fed-batch fermentation system.

It is well known that the carotenoids production by P. rhodozyma is typical non-growth associated type fermentation. It is thought that higher cell yield against the consumed carbon source (Yx/s) is obtained in the growth phase and lower Yx/s was obtained in the production phase. The present invention provides the new feeding strategies which comprise the exponential feeding methods combined with the carbon source concentration control and the feeding methods based on the carbon sources consumption rates in the aim of enhancing the cell growth extremely in the growth phase which possesses higher Yx/s, and regulating the cell growth and efficiently convert glucose to carotenoids in the production phase.

The present invention relates to a process for production of astaxanthin in high yield by P. rhodozyma utilizing the fed-batch fermentation system. Especially, the new feeding methods based on the cell growth, the carbon source consumption and the carotenoids productions were constructed.

The Phaffia strain is propagated by being transferred from a slant to 500 ml Erlenmeyer flasks containing 50 ml of nutrient medium in which the cells are cultured with shaking under sufficient aeration at 20-22° C. for 3 days. Thus this seed culture is transferred to 500 ml Erlenmeyer flasks containing 100 ml of nutrient medium, and incubated for 2 days on a rotary shaker under sufficient aeration at 20-22° C. Aliquots of these cell cultures are then, used to inoculate into the fermentors.

The seed culture is transferred to a 5 L fermentor containing 1.75 L of the nutrient medium. The culture was subjected to batch growth at 20-22° C. until a yeast dry matter content of 1 g/L was obtained. Thereafter, the solution of sugar supply was started and the fed-batch fermentation was performed at 20-22° C.

The nutrient medium basically contains glucose or sucrose as a carbon source and nitrogen sources supplemented with various vitamins and minerals in assimilable form. Typical of these vitamins and minerals are ammonium sulphate, potassium phosphate, magnesium sulphate, zinc sulphate, ferric ammonium sulphate, copper sulphate, inositol, pyridoxine hydrochloride, thiamine, calcium pantothenate, biotin, and the like. The combinations and concentrations of these materials, including the glucose and yeast extracts, can vary to convenience. If desired, an antifoam agent and/or other additives can also be incorporated into or used with the medium. The medium, which was fed to the fermentor in the fed-batch fermentation, contained a polysaccharide, e.g. glucose or sucrose.

The nutrient medium can contain polymerized forms of glucose, sucrose and other polysaccharides, molasses and corn syrup, glycerol and other polyols, carboxylic acids as the energy sources. Meanwhile, the nutrient medium can contain yeast extract, meat-extract, peptone, casein, corn steep liquor, urea, amino acidsnitrates, ammonium salts and the like as the nutrient sources.

The fermentor with the nutrient medium is sterilized by autoclaving. The working volume is not restricted and the fermentation can be operated from the small scale to the industrial large scale. The pH of the media is usually maintained between 4.5 and 7.0, and the temperature between 15-24° C. The medium is usually sparged with filter sterilized air, and it is continuously agitated. The strains are propagated in fermentors over a pH range of 4.5 to 7.0 controlled with $NH_4OH$ solution, NaOH solution or both. Temperature can be set at a range of from 15 to 24° C. and DO is controlled by agitation and airflow to between 10% and 90%.

1. Typical feeding method: A typical feeding method for nutrient media is disclosed in U.S. Pat. No. 6,015,684. During the growth phase, the feeding medium containing glucose or sucrose is fed to the main fermentor with the aim of reaching the specific growth rate of the yeast cells of μ: 0.01-0.10 $h^{-1}$.

And the feeding rate is gradually increased to so as not to accumulate the nutrient and ethanol in the culture broth. After the desired yeast solids is achieved and prior to the accumulation of the nutrient source, the feed rate is reduced to about 50% of the maximum feed rate during the growth phase. During this period of reduced nutrient source feed, namely the production phase, the yeast cells continue to produce astaxanthin, but the growth in the number of cells is restricted. Fermentations typically last 4-9 days, and they are sampled periodically for analysis of cell growth and astaxanthin production.

Specific glucose consumption rate (q) and the specific growth rate ($\mu$) can be calculated. $\mu$ is increased with q in the relationship between q and $\mu$. The slope $\mu/q$ means the cell yield against consumed glucose (Yx/s) as the equation (1).

$$\mu/q=\{(1/X)\cdot(dX/dt)\}/\{(1/X)\cdot(dS/dt)\}=dX/dS=Yx/s \quad (1)$$

X: cell concentration(g-dry cell/L)
S: carbon source concentration(g/L)

2. Exponential feeding method concerned with the C/N ratio: When the feeding rate is linearly increased in the growth phase, q is higher than the critical point, for example, as described in Example 1 and Yx/s is 0.200 to 0.500. On the other hand, when the feeding rate is linearly decreased in the production phase, Yx/s is lower than 0.200. Moreover, the astaxanthin production is increased and the maximum production rate is obtained in this period. It is well known that the astaxanthin production by P. rhodozyma is typical non-growth associated type fermentation. The higher Yx/s is obtained in the growth phase, and the lower Yx/s is obtained in the production phase. Therefore, in order to enhance the cell growth extremely in the growth phase, which possesses higher Yx/s, the exponential feeding method in the growth phase can be applied.

Furthermore, in the production phase, in order to restrict the cell growth and efficiently convert glucose to astaxanthin, the glucose concentration can be controlled in the production phase.

When the exponential feeding in the growth phase is applied, $\mu$ can be set at 0.01 to 0.1 hour$^{-1}$. The feeding rate(F) in the growth phase is expressed by following equation (2).

$$F=(q\cdot Vo\cdot Xo\cdot e^{\mu t})/(S_F-S) \quad (2)$$

Vo: initial volume (L)
Xo: initial cell concentration (g-dry cell/L)
$S_F$: carbon source concentration in feed medium (g/L)
S: carbon source concentration in culture broth (g/L)

Moreover, the relationship between the amount of NH$_4$OH addition and the glucose consumption based on the result of the typical fed-batch fermentation method (the control method) is applied for the glucose concentration control in the culture broth. It means the pH-stat method for glucose concentration control based on the NH$_4$OH addition (for maintaining pH). In the production phase, the glucose concentration can be controlled between 0 and 70 g/L, preferably between 0 and 10 g/L.

For instance, by using the 0 g/L glucose control, the final astaxanthin concentration can be higher than that in the control method. The maximum astaxanthin production rate can be more than 30.0% higher than that of the control method. As described in Example 3, when the glucose 0 g/L control was used, the C/N ratio in the production phase was 1.08 times higher than the glucose 2.0 g/L control, because the NH$_4$OH addition in the glucose 0 g/L control was smaller than that in the glucose 2.0 g/L control. It is known that the increment of the C/N ratio of feeding medium in the production phase enhances the astaxanthin production 1.5 times higher than the batch fermentation using the same amount of glucose. Therefore, it is thought that the astaxanthin production using the glucose 0 g/L control is larger than that using the glucose 2.0 g/L control.

Moreover, using NaOH solution as a pH control reagent in the production phase is the effective method for the astaxanthin production by the exponential feeding method with glucose 0 g/L control, because the C/N ratio in the production phase can be enhanced. The average astaxanthin productivity by using NaOH solution as a pH control reagent in the production phase with an aim to increase the C/N ratio in the production phase, can be more than 10.0% higher than by using NH$_4$OH solution. The exponential feeding method with glucose 0 g/L control using NaOH solution as a pH control reagent can be shortened more than 26.0% of the total fermentation period as compared to the control method. This exponential feeding method with glucose 0 g/L control can enhance the astaxanthin average productivity at least 13.0% higher than the control method.

3. The modified exponential feeding method: In order to enhance the total astaxanthin production and utilize higher astaxanthin average productivity of the exponential feeding method, the exponential feeding method can be improved by increasing the feeding amount of glucose and expanding the feeding period to the range of 10 to 50% longer. Effect of this expanding the feeding period method is 'the modified exponential feeding method' by enhancement of the feeding amount of glucose on astaxanthin fed-batch fermentation.

In the modified exponential feeding method, the exponential feeding is applied in the growth phase till the middle stage of the fermentation. After that, the feeding rate of the production phase is kept constant at the range of 10 to 100% of the maximum feeding rate in the growth phase. By using this modified exponential feeding method as described in Example 5, the final astaxanthin concentration was 5.8% higher than the concentration by the control method, and the total astaxanthin production was at least 29.0% higher than that by the control method. The modified exponential feeding method can enhance the astaxanthin content in dry cell more than 5.60% higher than the content by the control method.

4. Effect of the glucose concentration in the culture broth on the astaxanthin production: In the modified exponential feeding method, the glucose is accumulated in the culture broth at the middle of the fermentation period. It is known that the accumulation of glucose in culture broth reduces the astaxanthin production, especially the astaxanthin yield against carbon sources (e.g. glucose, sucrose, etc.). It is estimated that the ethanol formulation is induced by the Crabtree effect and the astaxanthin yield is decreased. From the relationship between the max glucose accumulation rate and the average specific astaxanthin production rate (p), p is gradually decreased to 71.0% of the average specific astaxanthin production rate at the no glucose accumulation phase, when the glucose begins to be accumulated in culture broth.

The accumulation of glucose in the culture broth inhibits the ability to produce astaxanthin per unit of cells. Therefore, for the purpose of enhancing the astaxanthin yield, it is necessary to construct the new feeding method for no glucose accumulating in the fermentation broth. Furthermore, in order to feed the glucose solution as large as possible, we have found the novel feeding method based on glucose consumption rate derived from the exponential feeding method.

5. The glucose consumption rate (GCR) feeding method: The GCR feeding method is based on the glucose consumption rate (GCR) in the fed-batch fermentation. The practical total glucose consumption profile can be derived from the exponential glucose feeding profile, e.g. as shown in Example 7.

Based on this feeding rate profile, the effect of the GCR feeding method can be investigated. In the GCR feeding method, the glucose concentration in the culture broth is able to keep around 0 g/L. In spite of the same volume of the nutrient medium, the final total astaxanthin production by using the GCR feeding method will be at least 8.0% higher than that by using the exponential feeding method. The average astaxanthin productivity by the GCR feeding method can be more than 7.0% higher than that by the exponential feeding method.

These results show that the GCR feeding method is more effective than the exponential feeding method in order to enhance the astaxanthin production. In the GCR feeding method, the feeding amount of glucose can be enhanced and the feeding period may be expanded.

6. The Max GCR feeding method: Furthermore, in order to enhance the feeding amount of glucose without accumulating the glucose in the fermentation, the new GCR feeding method based on the maximum glucose consumption rate (the Max GCR feeding method) can be constructed by investigating the effects of the feeding profile that combined GCR feeding and the constant feeding of keeping the maximum feeding rate in the GCR feeding method in the production phase.

The glucose accumulation in the culture broth affects the astaxanthin yield, and the yield against glucose used is lower than the yield by using the control method. If the new GCR feeding method is applied in order not to accumulate glucose in the fermentation broth, it is thought that the astaxanthin production yield can be remarkably enhanced. In order to investigate the Max GCR feeding method, the glucose consumption rate based on the feeding method that combined the GCR feeding with the constant feeding as described in Example 8 and the feeding rate profile based on the glucose consumption rate was calculated. In Example 9 the max glucose feeding rate profile calculated from the feeding method that combined the GCR feeding with the constant feeding as described in Example 8 is shown.

The max glucose feeding rate profile can be set valuable depending on compositions of the various nutrient media or fermentation conditions. Firstly, the Max GCR feeding method using $NH_4OH$ and NaOH solution for pH control can be applied based on the max glucose feeding rate profile. The total astaxanthin production by the Max GCR feeding method can be enhanced at least 4.0% higher than that by the control method. The maximum astaxanthin production rate can be obtained more than 20% higher than the rate by using the control method.

However, this method sometimes accumulates glucose in the culture broth. Therefore, in order to accumulate no glucose in the culture broth, the Max GCR feeding method using only $NH_4OH$ solution for pH control can be applied. By using this method, the glucose concentration in the culture broth can maintain 0 g/L during the whole fermentation period. The total astaxanthin production by this method can be enhanced more than 12% higher than that by the control method.

The astaxanthin production yield against glucose used by this Max GCR feeding method can be increased by at least 4.0% higher than that by the control method. The average astaxanthin production rate can be obtained more than 21% higher than the rate of the control method. Furthermore, this Max GCR feeding method using only $NH_4OH$ solution for pH control can shorten the fermentation period (at least 11% of the fermentation period can be cut down in the comparison with the control method) and enhance the astaxanthin productivity.

The present invention is illustrated by the following examples.

EXAMPLE 1

Typical Cultivation of P. rhodozyma ATCC96594 Mutant Strain for the Astaxanthin Production 1. Seed culture preparation: P. rhodozyma ATCC96594 mutant strain was used as seed strain. The Phaffia strain was propagated by being transferred from a slant to 500 ml Erlenmeyer flasks containing 50 ml of YM medium in which the cells were cultured with shaking under sufficient aeration at 20 to 22° C. for 3 days. This seed culture was transferred to 500 ml Erlenmeyer flasks containing 100 ml of YM medium, and incubated for 2 days on a rotary shaker under sufficient aeration at 20 to 22° C.

2. The fed-batch fermentation for astaxanthin production: 200 ml of the culture was transferred to a 5 L fermentor containing 1.75 L of the nutrient medium. The culture was subjected to batch growth at 20 to 22° C. until a yeast dry matter content of 1 g/L was obtained. Thereafter, the solution of sugar supply was started and the fed-batch fermentation was performed at 20 to 22° C.

The nutrient medium had the following composition: 20 g/L of molasses, 0.6 g/L of diammonium sulphate, 0.8 g/L of diammonium hydrogenphosphate and 0.125 g/L of magnesium sulphate which altogether were boiled up in the fermentor for 30 min together with a suitable amount of water (1.75 L in the 5 L propagation fermentor). The medium, which was fed to the fermentor in the fed-batch fermentation, contained 716.0 g/L of glucose or sucrose. All the chemicals were of food grade. The molasses were beet sugar molasses from Midwest agriculture, US.

The fermentation was carried out in the glass jar fermentor, D-type (Able, Tokyo, Japan) with a total volume of 5 L with a top drive system and temperature, pH, DO (dissolved oxygen) and exhaust gas monitor. The initial working volume and the feeding volume were 1.75 L and 2.0 L, respectively. The strains were propagated in fermentors at pH 5.5 controlled with 12.5 w/v % $NH_4OH$ solution and NaOH solution. Temperature was controlled at 20 to 22° C. and DO was controlled by agitation and airflow to between 10% and 90% saturation. During the growth phase, the feeding medium containing glucose or sucrose fed to the main fermentor with the aim of reaching the specific growth rate of the yeast cells of $\mu$: 0.04-0.05 $h^{-1}$. The feeding rate was gradually increased to so as not to accumulate the nutrient and ethanol in the culture broth.

Having achieved the desired yeast solids and prior to the accumulation of the nutrient source, the feed rate was reduced to about 50% of the maximum feed rate during the growth phase. During this period of reduced nutrient source feed, namely the production phase, the yeast cells continued to produce astaxanthin, but the growth in the number of cells was restricted. For example, in the production phase, the feeding rate was linearly reduced to about 50% of the maximum feed rate for about 100 hours.

EXAMPLE 2

Feeding Strategies Concerned with the Cell Growth Phase and the Astaxanthin Production Phase In the typical astaxanthin fed-batch fermentation described in example 1, the specific glucose consumption rate (q) and the specific growth rate ($\mu$) could be calculated and illustrated by a graph. When q and $\mu$ were 0.085 hours$^{-1}$ and 0.017 hour$^{-1}$, respectively, the slope of the line was drastically changed and critical point, (q, $\mu$)=(0.085, 0.017). The slope $\mu/q$ means the cell yield against consumed glucose (Yx/s) as the equation (1) as described above.

When the feeding rate was linearly increased in the growth phase, $\mu$ was higher than 0.085 hour$^{-1}$ and Yx/s was 0.213 to 0.405. On the other hand, when the feeding rate was linearly decreased in the production phase, Yx/s was lower than 0.201. Moreover, the astaxanthin production was increased and the maximum production rate was obtained in this period. It is well known that the astaxanthin production by P. rhodozyma is typical non-growth associated type fermentation.

The higher Yx/s was obtained in the growth phase, and the lower Yx/s was obtained in the production phase. Therefore, in order to enhance the cell growth extremely in the growth phase, which possessed higher Yx/s, and restrict the cell growth and efficiently convert glucose to astaxanthin in the production phase, the exponential feeding method in the growth phase and the glucose concentration control in the production phase were applied to the feeding strategies for the astaxanthin fed-batch fermentation.

EXAMPLE 3

Exponential Feeding Method Concerned with Effects of the C/N Ratio on the Astaxanthin Fed-batch Fermentation When the exponential feeding in the growth phase was applied, $\mu$ was set at 0.04 hour$^{-1}$. The feeding rate (F) in the growth phase is expressed by the equation (2) as described above.

In this investigation, q, Vo, Xo, $S_F$ and S were set at 0.08262 hour$^{-1}$, 1.75 L, 9.92 g-dry cell/L, 716.0 g/L, and 0 g/L, respectively. Consequently, F in the growth phase is calculated as the following equation (3), $$F=(0.08262 \cdot 1.75 \cdot 9.92 \cdot e^{0.04t})/(716.0-0)= 0.002003 \cdot e^{0.04t} \quad (3)$$

Moreover, the relationship between the amount of NH$_4$OH addition and the glucose consumption based on the result of Example 1 was investigated. Two linear relationships (I and II) between the amount of NH$_4$OH addition and the glucose consumption were obtained and the critical point (NH$_4$OH addition, Glucose consumption)=(3.95, 13.1) was introduced at 80 hours from the beginning of the fermentation. In the growth phase, the slope of the line was steep (I), in the production phase, the slope was gentle (II). Therefore, in order to control glucose 0 g/L in the production phase, the medium feeding method based on the NH$_4$OH addition (for maintaining pH) coming from the slope II, namely, pH-stat method for glucose concentration control was applied. The glucose concentration controls for the production phase were performed 0 and 2.0 g/L by 5 L jar fermentation in the same manner as Example 1. Besides, the glucose 2.0 g/L control was operated by the on-line glucose controller (the on-line biochemical controller BF-410: Able, Tokyo, Japan) in order to explore the effects of the C/N ratio on the astaxanthin production from the beginning of the feeding.

These two conditions were compared with the typical feeding method described in Example 1 (the control method). Comparison of the fermentation activity between the three conditions is shown in Table 1. The final astaxanthin concentration in the 0 g/L glucose control was 6.60% higher than that in the control method. The final astaxanthin concentration in the 2.0 g/L glucose control was 13.5% smaller than that in the control method.

The maximum astaxanthin production rate of the 0 g/L glucose control was 32.9% higher than that of the control method.

When the glucose 0 g/L control was used, the C/N ratio in the production phase was 1.08 times higher than the glucose 2.0 g/L control, because the NH$_4$OH addition in the glucose 0 g/L control was smaller than that in the glucose 2.0 g/L control. By the increment of the C/N ratio of feeding medium in the production phase, the astaxanthin production using the glucose 0 g/L control was larger than that using the glucose 2.0 g/L control.

TABLE 1

Fermentation activity in the astaxanthin fed-batch fermentation using a 5 L fermentor

| Status | Typical feeding method (Control) | Glucose 0 g/L control | Glucose 2.0 g/L control |
| --- | --- | --- | --- |
| Final ASTA conc. | 100 | 106.6 | 86.5 |
| Max ASTA production rate | 100 | 132.9 | 85.5 |

ASTA: astaxanthin; the data are expressed as relative values

EXAMPLE 4

New Feeding Method of Exponential Feeding and Glucose Concentration Control for the Astaxanthin Fed-batch Fermentation Moreover, the effects of C/N ratio on the exponential feeding method with glucose 0 g/L control were investigated by using NaOH solution as a pH control reagent in 5 L jar fermentations. The fermentations were performed in the same manner as in Example 1. In the case of the exponential feeding method, the glucose 0 g/L control in the production phase was carried out by the feeding method that the feeding rate is linearly decreased from 22.61 to 17.63 g-feed solution/hour. The average astaxanthin productivity by using NaOH solution as a pH control in production phase with an aim to increase the C/N ratio in the production phase, was 13.5% higher than by using NH$_4$OH solution.

Table 2 shows the comparison between the typical feeding method described in Example 1 (the control method) and the exponential feeding method by using NaOH solution as a pH control in the production phase in the astaxanthin production by fed-batch mode. The total fermentation period in the exponential feeding method was 41 hours shorter than that in the control method. The astaxanthin concentration by the exponential feeding method was 5.7% higher than that by the control method at 175 hours from the beginning of the fermentation. The astaxanthin average productivity in the exponential feeding method was 13.9% higher than that in the control method.

TABLE 2

Effect of the exponential feeding method by using NaOH solution as a pH control in the production phase on the astaxanthin production by the fed-batch mode

| Status | Typical feeding method (Control) | Exponential feeding method by using NaOH solution for the pH control |
|---|---|---|
| Final ASTA conc. at 175 th h | 100 | 105.7 |
| average ASTA production rate | 100 | 113.9 |

ASTA: astaxanthin; the data are expressed as relative values

EXAMPLE 5

Feeding Method of the Modified Exponential Feeding for the Astaxanthin Fed-batch Fermentation In order to enhance the total astaxanthin production and utilize higher astaxanthin average productivity of the exponential feeding method, the exponential feeding method was improved by increasing the feeding amount of glucose and expanding the feeding period from 117 hours to 156 hours. The effect of this expanding the feeding period method, in other words, 'the modified exponential feeding method' by enhancement of the feeding amount of glucose on astaxanthin fed-batch fermentation was investigated. In the modified exponential feeding method, the feeding rate of the production phase was kept at 19.7 g/hr till 186.5 hours from the beginning of the fermentation (156 hours from the beginning of the glucose feeding).

Table 3 shows the comparison between the typical feeding method described in Example 1 (the control method) and the modified exponential feeding method.

The final astaxanthin concentration by the modified exponential feeding method was 5.8% higher than that by the control method. The total astaxanthin production by the modified exponential feeding method was 29.3% higher than that by the control method. Although the glucose was accumulated in the culture broth from 98 hours to 192 hours by using the modified exponential feeding method, the fed glucose was completely consumed at the end of the fermentation. The astaxanthin content in dry cells in the modified exponential feeding method was 5.60% higher than that in the control method.

TABLE 3

Effect of the modified exponential feeding method on the astaxanthin production by the fed-batch mode

| Status | Typical feeding method (Control) | Modified exponential feeding method |
|---|---|---|
| Final ASTA conc. | 100 | 105.8 |
| Total amount of ASTA | 100 | 129.3 |
| ASTA content in dry cell | 100 | 105.6 |

ASTA: astaxanthin; the data are expressed as relative values

EXAMPLE 6

Effect of the Glucose Concentration in the Culture Broth on the Astaxanthin Fed-batch Fermentation As described in Example 5, the glucose was accumulated in the culture broth by using the exponential feeding method. The total astaxanthin production and yield were lower than the production by the control method described in Example 1. As the ethanol formulation may be induced by the Crabtree effect, the astaxanthin yield was decreased. Accordingly, the relationship between the max glucose accumulation rate and the average specific astaxanthin production rate (p) was investigated.

When the glucose began to be accumulated in culture broth, ρ was gradually decreased to 71.0% of the average specific astaxanthin production rate at the no glucose accumulation phase. These results show that the accumulation of glucose in culture broth inhibited the ability to produce astaxanthin per unit of cells. It was estimated that the ethanol formation was induced by the Crabtree effect and the astaxanthin yield was decreased.

EXAMPLE 7

Astaxanthin Fed-batch Fermentation by the New Feeding Method Based on the Practical Glucose Consumption Rate (The GCR Feeding Method)

For the purpose of enhancing the astaxanthin yield, it is necessary to construct the new feeding method for no glucose accumulating in the fermentation broth. Furthermore, in order to feed the glucose solution as large as possible, we studied the feeding method based on glucose consumption rate derived from the exponential feeding method.

The practical total glucose consumption profile differed from the exponential glucose feeding profile. Based on this result, the practical glucose consumption rate profile was calculated.

The practical profile of glucose consumption rate was expressed as a cubic equation by the multiple regression analysis. From the glucose consumption rate profile, a practical feeding rate profile showing glucose feeding pattern based on glucose consumption was established.

Based on this feeding rate profile, the effect of GCR feeding method was investigated. Table 4 shows the comparison between the exponential feeding method and the GCR feeding method. In the GCR feeding method, the glucose concentration in the culture broth was maintained around 0 g/L. In spite of the same condition that the initial volume was 1.75 L and the feeding volume was 2.00 L, the final total astaxanthin production by using the GCR feeding method was 8.99% higher than that by using the exponential feeding method. Furthermore, the fermentation period by the GCR feeding method was able to set 168 hour, which was the same period by the exponential feeding method. Then, the average astaxanthin productivity by GCR feeding method was 7.60% higher than that by the exponential feeding method.

TABLE 4

The effect of the modified exponential feeding method on the astaxanthin production by fed-batch mode

| Status | Modified exponential feeding method | GCR feeding method |
|---|---|---|
| Final ASTA conc. | 100 | 107.6 |
| Total amount of ASTA | 100 | 109.0 |
| Average ASTA productivity | 100 | 107.6 |

ASTA: astaxanthin; the data were expressed as relative values

EXAMPLE 8

Enhancement of the Feeding Amount of Glucose in the Astaxanthin Fed-batch Fermentation by the Modified GCR Feeding Method In the GCR feeding method, the feeding amount of glucose was enhanced and the feeding period was expanded to 156 hours. Table 5 shows the effects of the modified GCR feeding methods on astaxanthin production by fed-batch fermentation.

The modified GCR feeding method means the method that combines the GCR feeding method till 111 hours from the beginning of the glucose feeding and the feeding method of a linear decrement of the control method after 111 hours as described in Example 1.

The final total astaxanthin production by the modified GCR feeding method was 5.5% higher than that by the control method. Furthermore, the effects of the feeding profile that combined GCR feeding and the constant feeding of keeping the maximum feeding rate in the GCR feeding method, which was reached after 66th hour from the beginning of the glucose feeding. Namely, the GCR feeding method was used from the beginning of the glucose feeding to 66 hours, and the constant feeding which was kept 30.4 g-feed solution 1 hour of the max. feeding rate of the GCR feeding method, was used from 66 hours to 156 hours.

Table 5 also shows the results of the effects of the feeding method that combined the GCR feeding with the constant feeding. The final total astaxanthin production by this feeding method was 19.8% higher than that by the control method and about 14% higher than that by the modified GCR feeding method.

TABLE 5

The effects of the modified GCR feeding methods on astaxanthin production by fed-batch fermentation

| Status | Typical feeding method (Control) | Modified GCR feeding method | Modified GCR + constant feeding method |
|---|---|---|---|
| Total amount of ASTA | 100 | 105.5 | 119.8 |

ASTA: astaxanthin; the data were expressed as relative values

EXAMPLE 9

Astaxanthin Fed-batch Fermentation by the Max GCR Feeding Method

In Example 8 glucose in culture broth begun to accumulate gradually from 120 hours and the glucose concentration reached to 81.7 g/L at 192nd hour from the beginning of the fermentation. Finally, the glucose concentration was 33.6 g/L at the end of the fermentation. The glucose accumulation in culture broth affected the astaxanthin yield. Therefore, the new GCR feeding method based on the maximum glucose consumption rate (the Max GCR feeding method) was constructed. In order to investigate the Max GCR feeding method, the glucose consumption rate based on the feeding method that combined the GCR feeding with the constant feeding as described in Example 8 and the feeding rate profile based on the glucose consumption rate was calculated.

The max glucose feeding rate profile was calculated from the feeding method that combined the GCR feeding with the constant feeding as described in Example 8.

The maximum feeding rate calculated from the practical glucose consumption rate was 28.7 g/hr at 66 hours from the beginning of the glucose feeding. After 66 hours because of the decrement of the glucose consumption rate, the feeding rate had to be set to less than 19.0 g/hr in order to keep the glucose concentration around 0 g/L. Therefore, based on the max glucose feeding rate profile, Max GCR feeding method using $NH_4OH$ and NaOH solution for pH control was applied. The initial volume and the feeding volume were set at 1.50 L and 2.25 L, respectively.

Table 6 shows the effect of the Max GCR feeding method using $NH_4OH$ and NaOH solution for pH control on astaxanthin production by fed-batch fermentation. At 216 hours from the beginning of the fermentation, the total astaxanthin production by the Max GCR feeding method was 4.21% higher than that of the control method.

Furthermore, in the Max GCR feeding method, the maximum astaxanthin production rate calculated from 95 hours to 122 hours was and 20.1% higher than the rate by using the control method. However, glucose in the culture broth of the Max GCR feeding method using $NH_4OH$ and NaOH solution for pH control was accumulated 19.9 g/L at 175 hours from the beginning of the fermentation.

The astaxanthin production yield against glucose used by the Max GCR feeding method was lower than that by the control method, since the glucose was accumulated in the culture broth.

Next, in order to accumulate no glucose in the culture broth, the Max GCR feeding method using only $NH_4OH$ solution for pH control was established.

Table 7 shows the effect of Max GCR feeding method using only $NH_4OH$ solution for pH control on Astaxanthin production by fed-batch fermentation. In Table 7, the Max GCR feeding method using only $NH_4OH$ solution could maintain 0 g/L of the glucose concentration in the culture broth during the whole fermentation period. At 216 hours from the beginning of the fermentation, the total astaxanthin production by this method was 12.1% higher than that by the control method.

The astaxanthin production yield against glucose used by this Max GCR feeding method was 4.7% higher than that of the control method. In this Max GCR feeding method, the average astaxanthin production rate was 21.9% higher than the rate of the control method. From the total astaxanthin production profile, this Max GCR feeding method using only $NH_4OH$ solution for pH control in both the growth phase and the astaxanthin production phase could shorten the fermentation period (11.2% of the fermentation period was cut down in the comparison with the control method) and enhance the astaxanthin productivity.

TABLE 6

Effect of the Max GCR feeding method using $NH_4OH$ and NaOH solution for pH control on astaxanthin production by fed-batch fermentation

| Status | Typical feeding method (Control) | Max GCR feeding method by using NaOH and $NH_4OH$ for pH control |
|---|---|---|
| Total amount of ASTA | 100 | 104.2 |
| Max ASTA production rate | 100 | 120.1 |
| Max glucose accumulation in culture broth (g/L) | 0 | 19.9 |

ASTA: astaxanthin; the data were expressed as relative values

TABLE 7

Effect of the Max GCR feeding method using
NH₄OH and NaOH solution for pH control
on astaxanthin productioii by fed-batch fermentations

| Status | Typical feeding method (Control) | Max GCR feeding method by using NH₄OH solution for pH control |
|---|---|---|
| Total amount of ASTA | 100 | 112.1 |
| Max glucose accumulation in culture broth (g/L) | 0 | 0 |
| ASTA production yield | 100 | 104.7 |
| Final ASTA conc. | 100 | 108.3 |
| Average ASTA productivity | 100 | 121.9 |

ASTA: astaxanthin; the data were expressed as relative values

The invention claimed is:

1. A fermentation method of astaxanthin using Phaffia rhodozyma comprising the steps of: (a) in the growing phase, feeding of a nutrient medium containing glucose or sucrose based on the specific growth rate ($\mu$) of Phaffia rhodozyma cells, and (b) in the astaxanthin production phase, feeding of the nutrient medium based on the astaxanthin production rate, while keeping the glucose concentration in the fermentation broth at 0 g/L during the whole fermentation period.

2. The fermentation method according to claim 1, wherein the fermentation is carried out at a $\mu$ range between 0.01 and 0.10 h$^{-1}$.

3. The fermentation method according to claim 1, wherein the pH control reagent is NH₄OH solution, NaOH solution or both.

4. The fermentation method according to claim 1, wherein the fermentation is carried out at a pH between 4.5 and 7.0.

5. The fermentation method according to claim 1, wherein the fermentation is carried out at a temperature in the range of from 15 to 24° C.

6. The method according to claim 1, wherein the fermentation is carried out at DO between 10 and 90%.

7. The fermentation method according to claim 1, wherein the nutrient medium has at least one carbon energy source selected from the group consisting of polymerized forms of glucose, sucrose and other polysaccharides, molasses and corn syrup, glycerol and other polyols, and carboxylic acids, and, at least one nitrogen source selected from the group consisting of yeast extract, meat-extract, peptone, casein, corn steep liquor, urea, amino acid, nitrates, and ammonium salts.

8. The fermentation method according to claim 1, wherein the concentration of D-glucose or sucrose in the nutrient medium is from about 10 g/L to about 800 g/L.

9. The fermentation method according to claim 1, wherein the fermentation is carried out at gassing rates of about 0.01 to about 2.0 volume of gas/volume of medium/min. in the fermentation vessel.

10. The fermentation method according to claim 1, wherein Phaffia rhodozyma is Phaffia rhodozyma ATCC96594.

* * * * *